(12) United States Patent
Cowan

(10) Patent No.: US 8,956,415 B2
(45) Date of Patent: Feb. 17, 2015

(54) VERTEBRAL IMPLANT

(75) Inventor: John A. Cowan, Rome, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 335 days.

(21) Appl. No.: 13/208,158

(22) Filed: Aug. 11, 2011

(65) Prior Publication Data

US 2012/0041494 A1 Feb. 16, 2012

Related U.S. Application Data

(60) Provisional application No. 61/373,852, filed on Aug. 15, 2010, provisional application No. 61/419,225, filed on Dec. 2, 2010.

(51) Int. Cl.

| A61F 2/44 | (2006.01) |
| A61B 17/70 | (2006.01) |
| A61B 17/17 | (2006.01) |
| A61B 17/80 | (2006.01) |
| A61F 2/46 | (2006.01) |
| A61B 17/34 | (2006.01) |
| A61F 2/30 | (2006.01) |

(52) U.S. Cl.
CPC ......... *A61B 17/7059* (2013.01); *A61B 17/1757* (2013.01); *A61B 17/8042* (2013.01); *A61B 17/808* (2013.01); *A61F 2/4455* (2013.01); *A61F 2/4611* (2013.01); *A61B 17/3421* (2013.01); *A61B 17/7064* (2013.01); *A61B 17/7071* (2013.01); *A61B 17/809* (2013.01); *A61F 2002/30578* (2013.01); *A61F 2002/30604* (2013.01); *A61F 2002/30785* (2013.01); *A61F 2002/30841* (2013.01); *A61F 2002/4475* (2013.01)
USPC ...................... 623/17.16; 623/17.11; 606/246

(58) Field of Classification Search
USPC ...................... 623/17.11–17.13, 17.15–17.16
See application file for complete search history.

(56) References Cited

U.S. PATENT DOCUMENTS

| 4,501,269 A | 2/1985 | Bagby |
| 4,641,370 A | 2/1987 | Oyamada |
| 4,904,261 A | 2/1990 | Dove |
| 4,955,908 A | 9/1990 | Frey |
| 5,192,327 A | 3/1993 | Brantigan |
| 5,290,312 A | 3/1994 | Kojimoto et al. |
| 5,306,309 A | 4/1994 | Wagner et al. |
| 5,388,691 A | 2/1995 | White |
| 5,522,899 A | 6/1996 | Michelson |
| 5,776,199 A | 7/1998 | Michelson |
| 5,888,223 A | 3/1999 | Bray, Jr. |
| 5,888,224 A | 3/1999 | Beckers et al. |
| 6,066,175 A | 5/2000 | Henderson et al. |
| 6,086,613 A | 7/2000 | Camino et al. |
| 6,106,557 A | 8/2000 | Robioneck et al. |

(Continued)

*Primary Examiner* — Todd Manahan
*Assistant Examiner* — Jessica Weiss

(57) ABSTRACT

An implant and method for attaching to vertebral members with the implant including a plate and a cage. The plate is configured to be positioned against and anchored to the bodies of the vertebral members. The plate may also extend into the intervertebral space between the vertebral members. The cage extends outward from the plate and is positioned within the intervertebral space. The implant provides a low profile that is positionable between the bodies of the vertebral members and the lamina/pars/facet joint. The implant may be implanted utilizing a lateral access to the spine. The implant and method may further include just the plate without the cage.

20 Claims, 17 Drawing Sheets

(56) References Cited

U.S. PATENT DOCUMENTS

| | | |
|---|---|---|
| 6,120,503 A | 9/2000 | Michelson |
| 6,152,927 A * | 11/2000 | Farris et al. .................. 606/287 |
| 6,156,037 A | 12/2000 | LeHuec et al. |
| 6,231,610 B1 | 5/2001 | Geisler |
| 6,235,059 B1 | 5/2001 | Benezech et al. |
| 6,342,074 B1 | 1/2002 | Simpson |
| 6,432,106 B1 | 8/2002 | Fraser |
| 6,447,544 B1 | 9/2002 | Michelson |
| 6,572,619 B2 | 6/2003 | Santille |
| 6,572,654 B1 | 6/2003 | Santilli |
| 6,579,290 B1 | 6/2003 | Hardcastle et al. |
| 6,613,091 B1 | 9/2003 | Zdeblick et al. |
| 6,629,998 B1 | 10/2003 | Lin |
| 6,682,561 B2 | 1/2004 | Songer et al. |
| 6,706,070 B1 | 3/2004 | Wagner et al. |
| 6,749,636 B2 | 6/2004 | Michelson |
| 6,793,679 B2 | 9/2004 | Michelson |
| 6,837,905 B1 | 1/2005 | Lieberman |
| 6,899,734 B2 | 5/2005 | Castro et al. |
| 6,926,737 B2 | 8/2005 | Jackson |
| 6,962,606 B2 | 11/2005 | Michelson |
| 6,972,019 B2 | 12/2005 | Michelson |
| 6,984,234 B2 | 1/2006 | Bray |
| 6,984,245 B2 | 1/2006 | McGahan et al. |
| 6,991,653 B2 | 1/2006 | White et al. |
| 7,014,659 B2 | 3/2006 | Boyer, II et al. |
| 7,077,864 B2 | 7/2006 | Byrd, III et al. |
| 7,112,222 B2 * | 9/2006 | Fraser et al. ............... 623/17.11 |
| 7,135,043 B2 | 11/2006 | Nakahara et al. |
| 7,172,627 B2 | 2/2007 | Fiere et al. |
| 7,232,464 B2 | 6/2007 | Mathiseu et al. |
| 7,300,441 B2 | 11/2007 | Haid et al. |
| 7,594,931 B2 | 9/2009 | Louis et al. |
| 7,658,766 B2 | 2/2010 | Melkent et al. |
| 7,776,095 B2 | 8/2010 | Petermab et al. |
| 7,819,903 B2 | 10/2010 | Fraser et al. |
| 7,846,207 B2 | 12/2010 | Lechmann et al. |
| 7,850,731 B2 | 12/2010 | Brittan et al. |
| 7,862,616 B2 | 1/2011 | Lechmann et al. |
| 7,875,076 B2 | 1/2011 | Mathieu et al. |
| 7,887,595 B1 | 2/2011 | Pimenta |
| 8,114,162 B1 * | 2/2012 | Bradley ..................... 623/17.16 |
| 8,709,083 B2 * | 4/2014 | Duffield et al. ............ 623/17.16 |
| 2003/0191531 A1 | 10/2003 | Berry et al. |
| 2004/0092929 A1 | 5/2004 | Zindrick |
| 2004/0249377 A1 * | 12/2004 | Kaes et al. ...................... 606/61 |
| 2005/0124993 A1 | 6/2005 | Chappuis |
| 2006/0030851 A1 | 2/2006 | Bray et al. |
| 2007/0106384 A1 * | 5/2007 | Bray et al. ................. 623/17.11 |
| 2007/0250167 A1 * | 10/2007 | Bray et al. ................. 623/17.11 |
| 2007/0255414 A1 | 11/2007 | Melkent |
| 2009/0192613 A1 * | 7/2009 | Wing et al. ................ 623/17.11 |
| 2009/0210062 A1 | 8/2009 | Thalgott et al. |
| 2010/0057206 A1 | 3/2010 | Duffield et al. |
| 2010/0070037 A1 | 3/2010 | Parry et al. |
| 2010/0217393 A1 | 8/2010 | Theofilos |
| 2011/0004253 A1 | 1/2011 | Fraser et al. |
| 2011/0040382 A1 | 2/2011 | Muhanna |

\* cited by examiner

VERTEBRAL IMPLANT

RELATED APPLICATIONS

The present application claims priority to U.S. applications 61/373,852 filed Aug. 15, 2010 and 61/419,225 filed Dec. 2, 2010, each of which is incorporated by reference herein in its entirety.

BACKGROUND

Diseases of the vertebral column requiring surgical intervention are relatively common. A variety of conventional devices exist for specific areas of the vertebral column to provide restoration, decompression, or stabilization of the spine due to variety of different spinal pathologies, including degeneration, trauma, tumor, infection, congenital abnormalities or the like. An example of an implantable interbody device is a cage and plate. The cage may be inserted in the intervertebral space defined between two adjacent vertebral members and the plate is secured to the vertebral members via a plurality of anchors. The conventionally known devices vary in size, shape, materials used, and insertion techniques.

Various approaches may be utilized to implant an interbody device, such as an anterior lumbar fusion approach or a posterior lumbar fusion approach. Preferably, a minimally invasive surgical technique is used to reduce trauma to surrounding tissue and improving safety and efficacy.

Thus, there is a need in the art for an easier to use, safer, more cost effective vertebral implant and method of implanting a vertebral implant that includes positioning and securing the vertebral implant to the vertebral members.

SUMMARY

The present application is directed to vertebral implants for attaching to vertebral members. One implant includes a plate with an inner side configured to be positioned towards the vertebral members. The inner side includes a first contact section configured to contact against a body of the superior vertebral member and a second contact section configured to contact against a body of the inferior vertebral member. The implant includes a plurality of legs that each extend outward from and are spaced apart along the inner side. Each of the legs is configured to fit within an intervertebral space formed between the vertebral members. The plurality of legs are spaced apart along the inner side by a gap. A ledge is formed at the second contact section and positioned away from a gap formed between the plurality of legs. The ledge extends outward beyond the second contact section and is configured to contact against an endplate of the inferior vertebral member. At least one aperture extends through the second contact section to receive an anchor. A cage is positioned in the gap between the legs and extends outward from the inner side of the plate and is configured to fit within the intervertebral space. The first and second contact sections of the inner side may be aligned, and the inner side may further include a third contact section positioned in the gap to contact against the cage. The third contact section may be misaligned with the first and second contact sections and positioned outward toward the cage more than the first and second contact sections.

The implant may also include a plate with an side configured to be positioned towards the vertebral members and an opposing outer side. The plate also includes a superior side configured to be positioned along the first vertebral member and an opposing inferior side configured to be positioned along the second vertebral member. First and second elbows are positioned on the inner side and each include a first face configured to contact against a body of one of the vertebral members and a second face that extends outward from the first face and away from the outer side of the plate to contact against an endplate of one of the vertebral members. The elbows are spaced apart along the inner side by a gap and oriented in opposing directions with the second face of the first elbow facing towards the superior side of the plate to face towards an endplate of the first vertebral member and the second face of the second elbow facing towards the inferior side of the plate to face towards an endplate of the second vertebral member. A first protrusion extends outward from the inner side of the plate and is positioned in the gap and includes an outer surface that aligns with the second contact surface of the first elbow to face towards the endplate of the first vertebral member. A second protrusion extends outward from the inner side of the plate and is positioned in the gap and includes an outer surface that aligns with the second contact surface of the second elbow to face towards the endplate of the second vertebral member. An aperture extends through the plate to receive an anchor to attach the plate to one of the first and second vertebral members. A cage is positioned between the protrusions and has a length to extend outward from the inner side of the plate beyond the protrusions and is configured to fit within the intervertebral space. The first faces of each of the first and second elbows may be aligned within a common plane.

Another implant includes a plate with an inner side configured to be positioned towards the vertebral members and an opposing outer side. The plate includes a superior side configured to be positioned along the first vertebral member and an opposing inferior side configured to be positioned along the second vertebral member. The plate also includes lateral sides that extend between the superior and inferior sides with the plate having a greater length measured between the superior and inferior sides than a width measured between the lateral sides. First and second elbows are positioned on the first side and spaced apart along the length. Each of the elbows includes a first face configured to contact against a body of one of the vertebral members and a second face that extends outward from the first face of the plate to face towards an endplate of one of the vertebral members when the plate is implanted in the patient. The elbows are oriented in opposing directions with the second face of the first elbow facing towards the superior side of the plate and the second face of the second elbow facing towards the inferior side of the plate. A first protrusion extends outward from the first side of the plate and is positioned between the elbows and includes an outer surface that aligns with the second contact surface of the first elbow to face towards the endplate of the first vertebral member. A second protrusion extends outward from the first side of the plate and is positioned between the elbows and includes an outer surface that aligns with the second contact surface of the second elbow to face towards the endplate of the second vertebral member. An aperture extends through the plate from the outer side to the inner side to receive an anchor to attach the plate to one of the first and second vertebral members.

The application also includes methods of attaching an implant to first and second vertebral members. One method includes positioning a plate across an intervertebral space with a superior portion of the plate extending over the first vertebral member and an inferior portion of the plate extending over the second vertebral member. The method includes positioning the superior portion with a contoured shape under nerve roots at the first vertebral member. The method includes inserting a first portion of a first side of the plate into the intervertebral space and contacting a first contact surface on the superior portion of the plate against a body of the first vertebral member and contacting a second contact surface on the inferior portion of the plate against a body of the second vertebral member. The method includes positioning a cage that extends from the first side of the plate within the intervertebral space. The method also includes inserting a first anchor through the plate and into the endplate of the first vertebral member, and inserting a second anchor through the plate and into a pedicle of the second vertebral member.

Another method includes aligning a plate within the patient with the plate having an elongated shape with a length that extends through superior and inferior portions being greater than a width that extends through lateral sides. The method includes positioning the superior portion of the plate over the first vertebral member with a contoured shape of the superior portion positioned away from nerve roots. The method includes positioning an inferior portion of the plate over a remaining section of a pedicle of a second vertebral member. The method includes contacting a first contact surface on the superior portion of the plate against a body of the first vertebral member. The method includes contacting a second contact surface on the inferior portion of the plate against the second vertebral member. The method also includes inserting a first anchor through the plate and into the endplate of the first vertebral member, and inserting a second anchor through the plate and into the remaining section of the pedicle of the second vertebral member.

Other features and advantages of the present disclosure will be readily appreciated, as the same becomes better understood after reading the subsequent description taken in conjunction with the accompanying drawings.

DETAILED DESCRIPTION

The present application is directed to a vertebral implant and methods of implanting the vertebral implant relative to vertebral members. One application of the implant is for the fusion of two vertebral members. This implant 10 generally includes a plate 20 and a cage 30. As illustrated schematically in FIG. 1, the plate 20 is positioned against and anchored to the vertebral members 201, 202. The plate 20 may also extend into the intervertebral space between the vertebral members 201, 202. The cage 30 extends outward from the plate 20 and is positioned within the intervertebral space. The implant 10 provides a low profile that is implantable between the bodies of the vertebral members 201, 202 and the lamina/pars/facet joint. The implant 10 may be implanted utilizing a posterior far lateral access to the spine. Another application of the implant 10 includes the plate 20 being used without the cage 30.

Figure 2:
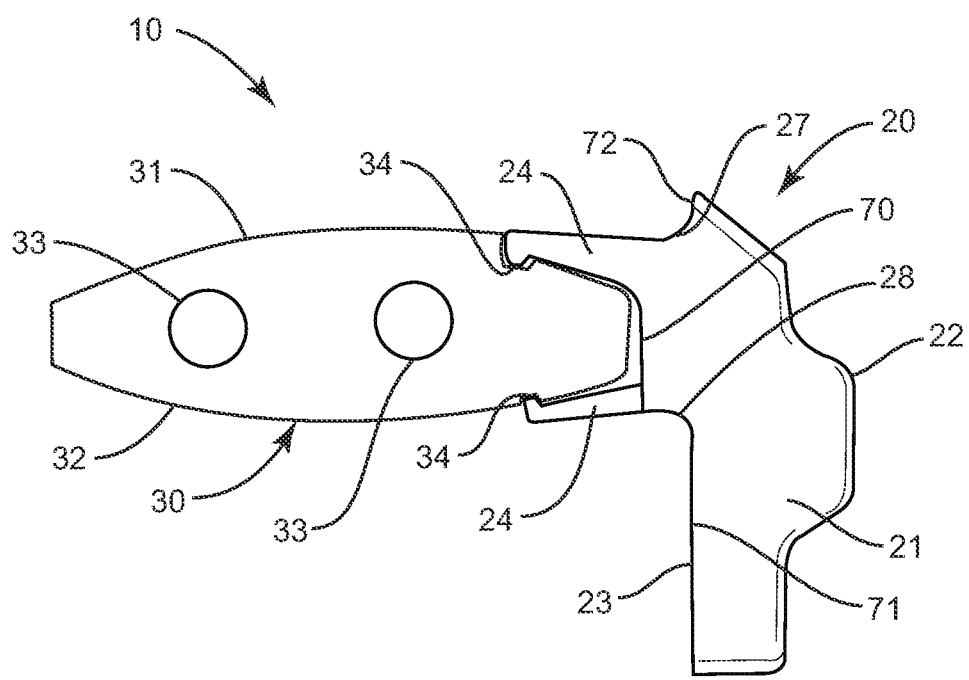
FIG. 2 is a side view of an implant.
Figure 5:
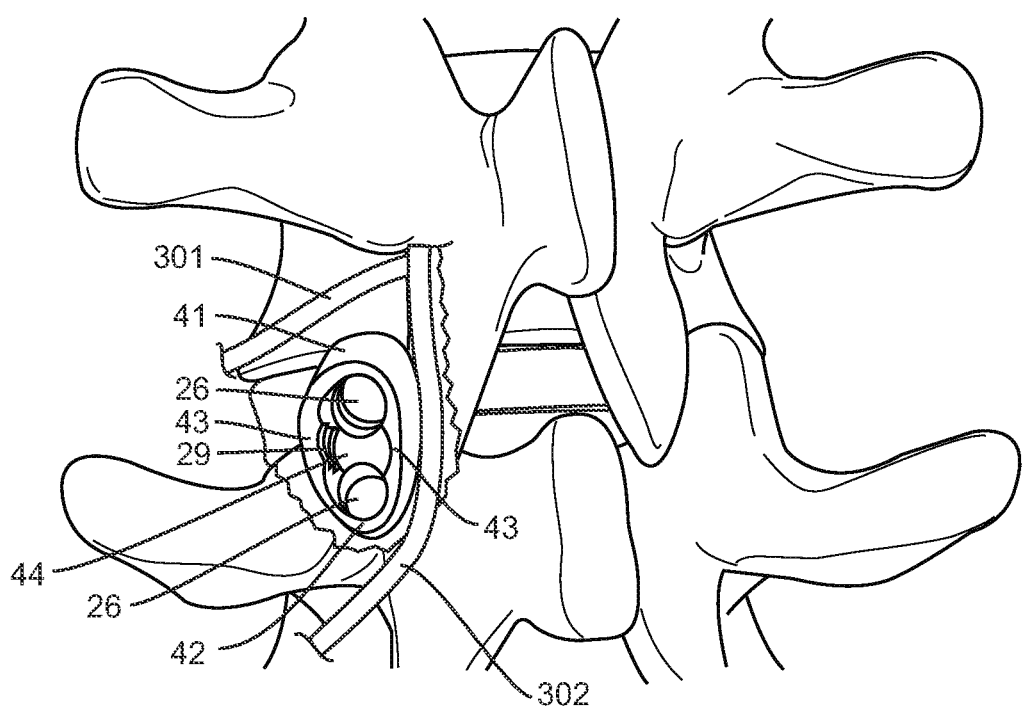
FIG. 5 is a front view of a plate in the intended anatomic position.

FIG. 2 illustrates an implant 10 that includes a plate 20 and a cage 30. The plate 20 includes a body 21 with an outer side 22 configured to face outward away from the vertebral members and an opposing inner side 23 that faces towards the vertebral members when the implant 10 is implanted into the patient. The plate 20 includes a length between inferior and superior sides to span across the intervertebral space and along portions of the bodies of the vertebral members. The plate has a width between the opposing lateral sides. As illustrated in FIG. 5, the width is less than the length for the implant 10 to be positioned against the vertebral members in the desired location. The plate 20 also includes a reduced height measured between the sides 22, 23 to be recessed within the vertebral body space so the plate 20 does not protrude from the dorsal part of the lamina/pars/facet joint of the vertebral members.

The first outer side 22 faces outward away from the vertebral members. The first outer side 22 may be shaped and configured to conform to the anatomy and reduce the profile of the plate 20.

The inner side 23 faces inward towards the vertebral members. The inner side 23 is configured to contact against the bodies of the vertebral members and may also extend into the intervertebral space. As illustrated in FIG. 2, the inner side 23 includes first and second sections 70, 71 that are offset from one another along the height of the plate 20.

A ledge 28 is formed at the second section 71 and is configured to engage with an endplate of the inferior vertebral member when the plate 20 is implanted into the patient as will be explained in detail below. The ledge 28 may include a rounded elbow at the transition with the second section 71. The ledge 28 contacts against the endplate of the inferior vertebral member with the second section 71 contacting against the body of the inferior vertebral member 202. In one embodiment, the ledge 28 includes a surface that is substantially perpendicular to the first section 71. In one embodiment, the outer surface of the inferior leg 24 is aligned with the ledge 28.

Another ledge 27 may be positioned towards the superior end of the cage 20. Ledge 27 is spaced apart from ledge 28 along the inner side 23. The ledge 27 may include a rounded elbow that transitions into a third section 72. The ledge 27 is configured to face towards the endplate of the superior vertebral member when the implant 10 is positioned in the patient. The ledge 27 may contact against the endplate of the superior member, or may be spaced away from the endplate depending upon the size of the implant 10 relative to the intervertebral space. In one embodiment, the outer surface of the superior leg 24 is aligned with the ledge 27.

The sections 71, 72 may be aligned along a common plane. Section 70 positioned between the legs 24 is offset from the sections 71, 72.

Figure 3:
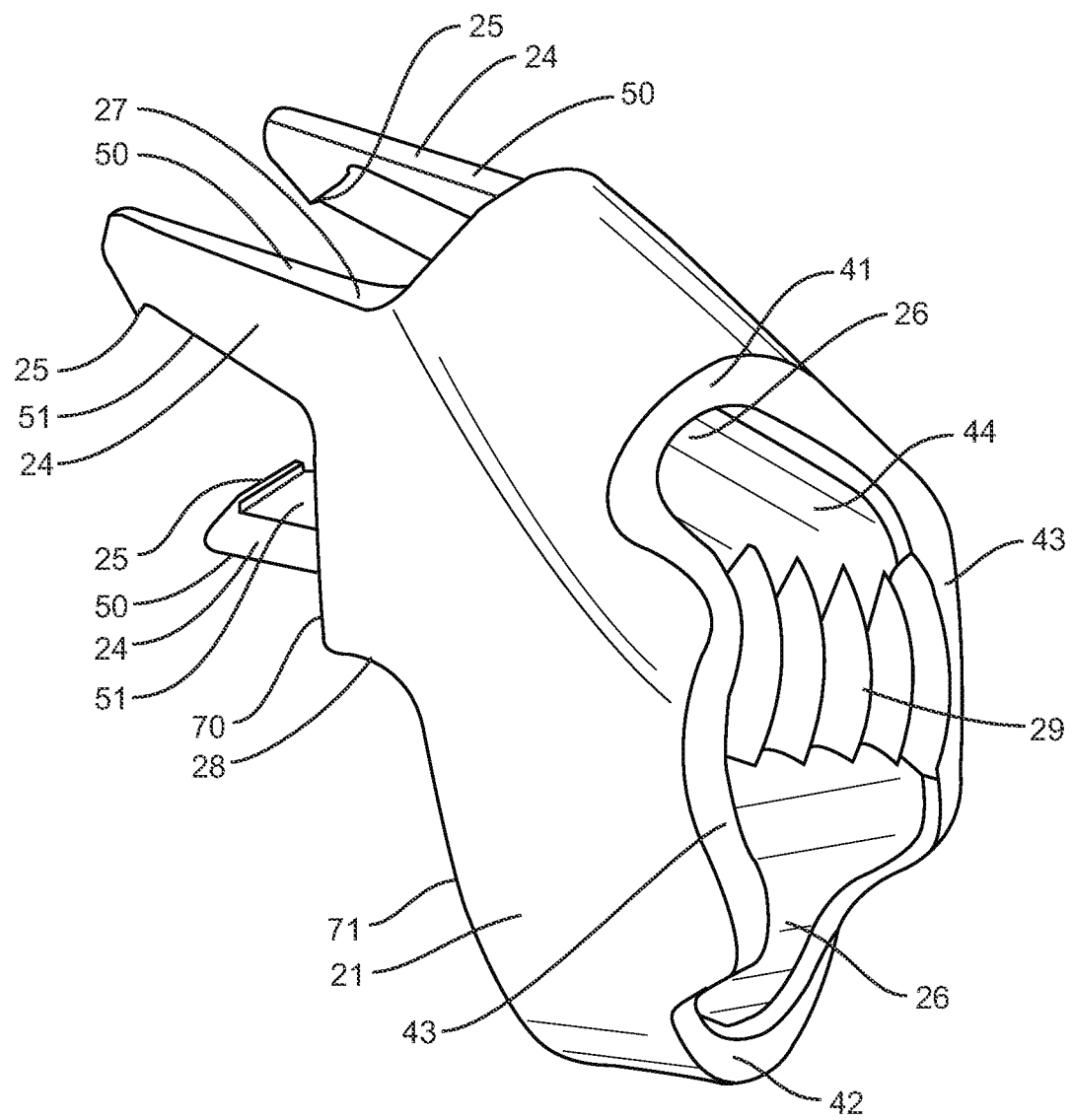
FIG. 3 is a perspective view of a plate.
Figure 4:
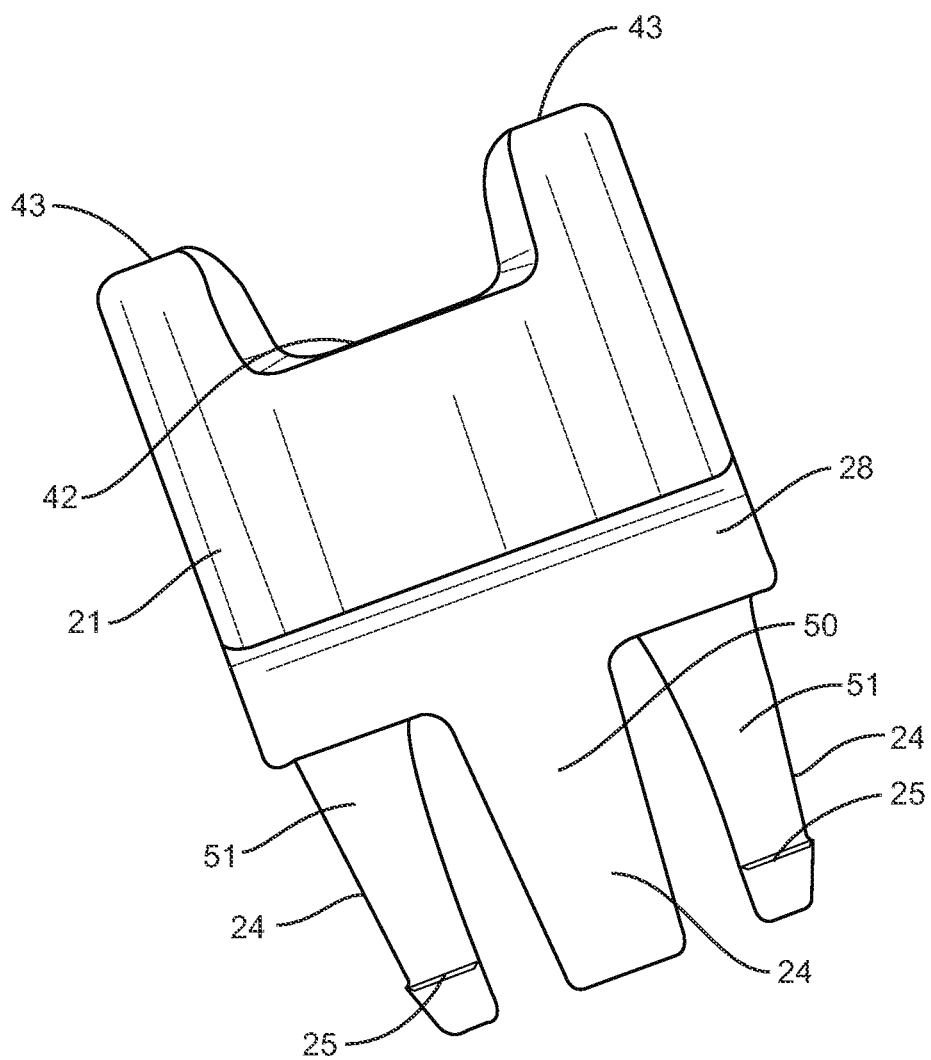
FIG. 4 is a bottom view of a plate.

The legs 24 extend outward from the inner side 23 and are configured to extend into the intervertebral space and position the plate 20 relative to the vertebral members. This provides reproducibility of insertion and protection of adjacent nerve roots. The legs 24 may also be configured to receive the cage 30. The legs 24 may include the same or different shapes and/or sizes. In one embodiment, the plate 20 includes three legs 24 with two superior legs and one inferior leg 24. FIGS. 3 and 4 best illustrate an embodiment with two superior legs 24 that are spaced at the same point along the inner side 23 and on opposing lateral sides of the plate 20, and a single inferior leg 24 centrally positioned on the plate 20. In embodiments with inferior and superior legs 24, the legs 24 are separated by a distance to position the plate relative to the vertebral members. The distance may vary depending upon the location along the spine where the plate 20 is being implanted, and the anatomy of the patient.

The outer surfaces of the legs 24 are configured to contact against the endplates of the vertebral members. The legs 24 include a length and width to provide a contact area for contacting the vertebral members. The outer surfaces 50 of the legs 24 may be relatively smooth to facilitate sliding the legs 24 into the intervertebral space. In embodiments where the plate 20 is used with a cage 30, the inner surfaces 51 are configured to receive the cage 30. The inner surfaces 51 may include tabs 25 towards the exposed ends that extend inward to engage with the cage 30. The tabs 25 may include a tapering width that tapers towards the end. The tabs 25 may also include an opposing lip that engages with the cage 30.

The ledges 27, 28 are spaced apart by a gap along the second side of the inner side 23 of the plate 20. The ledges 27, 28 face in opposite directions with the ledge 27 facing towards a superior end of the plate 20 to contact against the first vertebral member and the ledge 28 facing towards an inferior end to contact against the second vertebral member. As illustrated in FIG. 2, the ledges 27, 28 may extend into elbows formed on the first side. The first elbow at ledge 27 is configured to abut against the corner of the first vertebral member and the second elbow at ledge 28 to abut against the corner of the second vertebral member. The elbows may include rounded corners to facilitate contact with the vertebral members and prevent damage.

As best illustrated in FIG. 5, the plate 20 includes a superior section 41, an inferior section 42, and opposing intermediate sections 43. These sections 41, 42, 43 are spaced apart to form a central recess 44. Although the illustrated plate 20 is generally oval in shape, the plate 20 can have a variety of other shapes, such as, rectangular, square, circular, or the like.

The plate 20 is further configured to facilitate implantation into the spine and coupling of adjacent vertebrae. The superior section 41 includes an angled and contoured surface to minimize contact with the exiting and traversing nerve roots 301, 302 when the plate 20 is positioned in the patient.

One or more apertures 26 may extend through the plate 20 in the recess 44 to receive anchors 90 for securing the plate 20 to the vertebral members. In one embodiment as illustrated in FIG. 5, two apertures 26 that extend through the plate 20 at the bottom of the recess 44. In another embodiment, the plate 20 includes more than two apertures 26. Each aperture is sized to receive one or more anchors 90.

The apertures 26 are configured for the anchors 90 to be positioned at different angles. The apertures 26 may be formed at an angle through the plate 20 and/or may be sized for the anchors 90 to be positioned at various angles. For example, the superior aperture 26 may provide for the anchor 90 to be positioned at a diverging angle of between 25-40 degrees from a centrally located instantaneous axis of rotation of the vertebral disc space, to strengthen attachment and performance of the device. In one embodiment, the plate 20 is configured with an inferior aperture 26 aligned and configured for a first anchor 90 to be positioned at the partially removed pedicle of the inferior vertebral member and a superior aperture 26 aligned and configured to be positioned in the endplate of the superior vertebral member.

Figure 6:
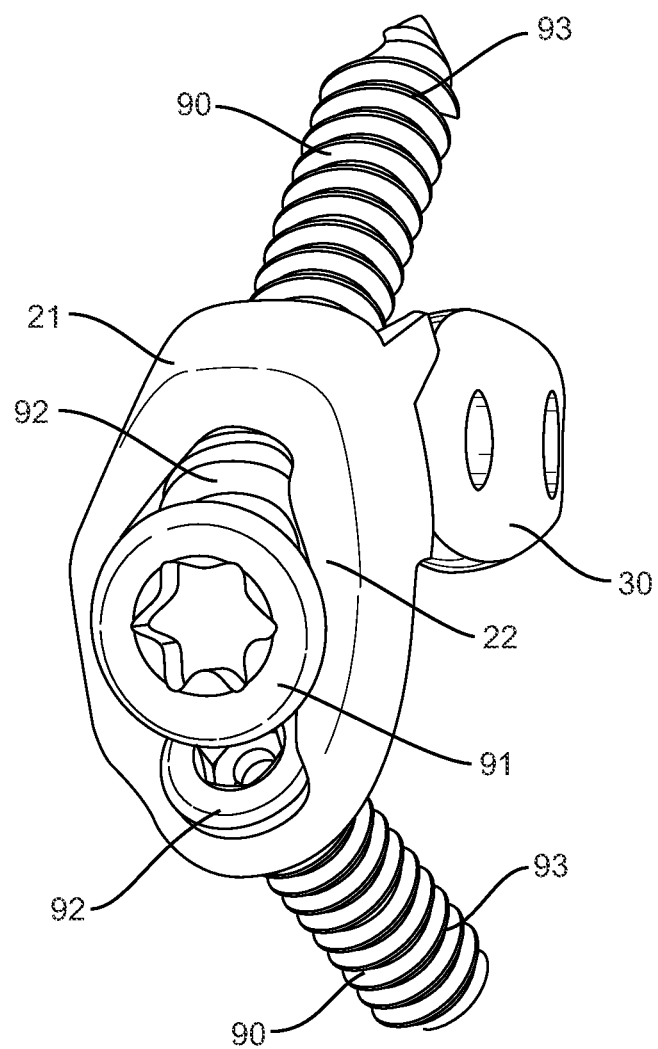
FIG. 6 is a front perspective view of an implant with anchors and a securing device.

The recess 44 may further include an outer receptacle 29 with threads to receive a securing device 91 as illustrated in FIGS. 5 and 6. The securing device 91 includes a head that extends over the anchors and a shank that engages with the threaded outer receptacle 29. FIGS. 5 and 6 include an embodiment with the plate 20 configured to receive two anchors 90 that may be positioned at various angular trajectories and the securing device 91 extending over the heads to prevent back-out. Other embodiments may include multiple receptacles 29 to receive multiple securing devices 91. In one specific embodiment, a first securing device 91 is positioned in a first receptacle 29 at a superior section of the plate 20 to secure a first anchor 90, and a second securing device 91 is positioned in a second receptacle 29 at an inferior section of the plate 20 to secure a second anchor 90.

The plate 20 can be fabricated from various materials, such as, plastic, metal, alloys, or the like, and can be magnetic resonance imaging (MRI) compatible.

The anchors 90 include a head portion 92 and a shank 93. The head 92 is wider than the shank 93 and configured to seat within the recess 44 in the plate 20. The shank 93 can have a predetermined dimension (e.g., length, size, shape, etc.) depending on factors, such as, the location of implant 10, the purpose of implant 10, or the like. The shank 93 can also be designed to have varying attributes along its length. For example, a portion of the shank 93 may be threaded, and the threaded portion may have a predetermined thread pitch, thread length. Likewise, a non-threaded portion or lag areas may have a predetermined length.

The cage 30 is configured to attach to the plate 20 and be positioned within the intervertebral space between the vertebral members. The cage 30 includes a superior side 31 configured to contact against the endplate of the superior vertebral member and an inferior side 32 configured to contact against the endplate of the inferior vertebral member. The height of the cage 30 measured between the sides 31, 32 may vary depending upon spinal level and anatomy of the patient.

The cage 30 may be attached to the plate 20 in various manners. One or both sides 31, 32 may include receptacles 34 that align with the legs 24 of the plate 20. The receptacles 34 include edges that engage with the tabs 25 on the legs 24 to maintain attachment. The cage 30 may also include apertures 33 that align with the apertures 26 in the plate 20 such that the anchors 90 extend through both the plate 20 and cage 30 to attach the members together. The posterior end of the cage 30 may be shaped to abut against or be in proximity to the plate 20.

The cage 30 may include a variety of shapes, including circular, square, oval, and the like. The cage 30 may include an annular shape with a cavity that is open at one or both of the superior and inferior sides 31, 32. The cavity is designed to receive various materials, such as, spongy bone, bone material, or the like, and to accommodate bone growth. The surfaces and walls of the cage 30 can also have a particular texture (e.g., smooth, serrated, toothed, grooved, etc.) to facilitate gripping, attachment, or the like.

The cage 30 may be formed from a conventional material, such as PEEK or donor bone.

The implant 10 may be inserted into a patient using an insertion device 60. The insertion device 60 may be utilized for various purposes, including a guide for inserting and securing the implant 10, as an impactor device, a guide for a tool, a screw guide, and the like. The multifunctional insertion device 60 may be fabricated from a radiotranslucent material or the like.

Figure 7:
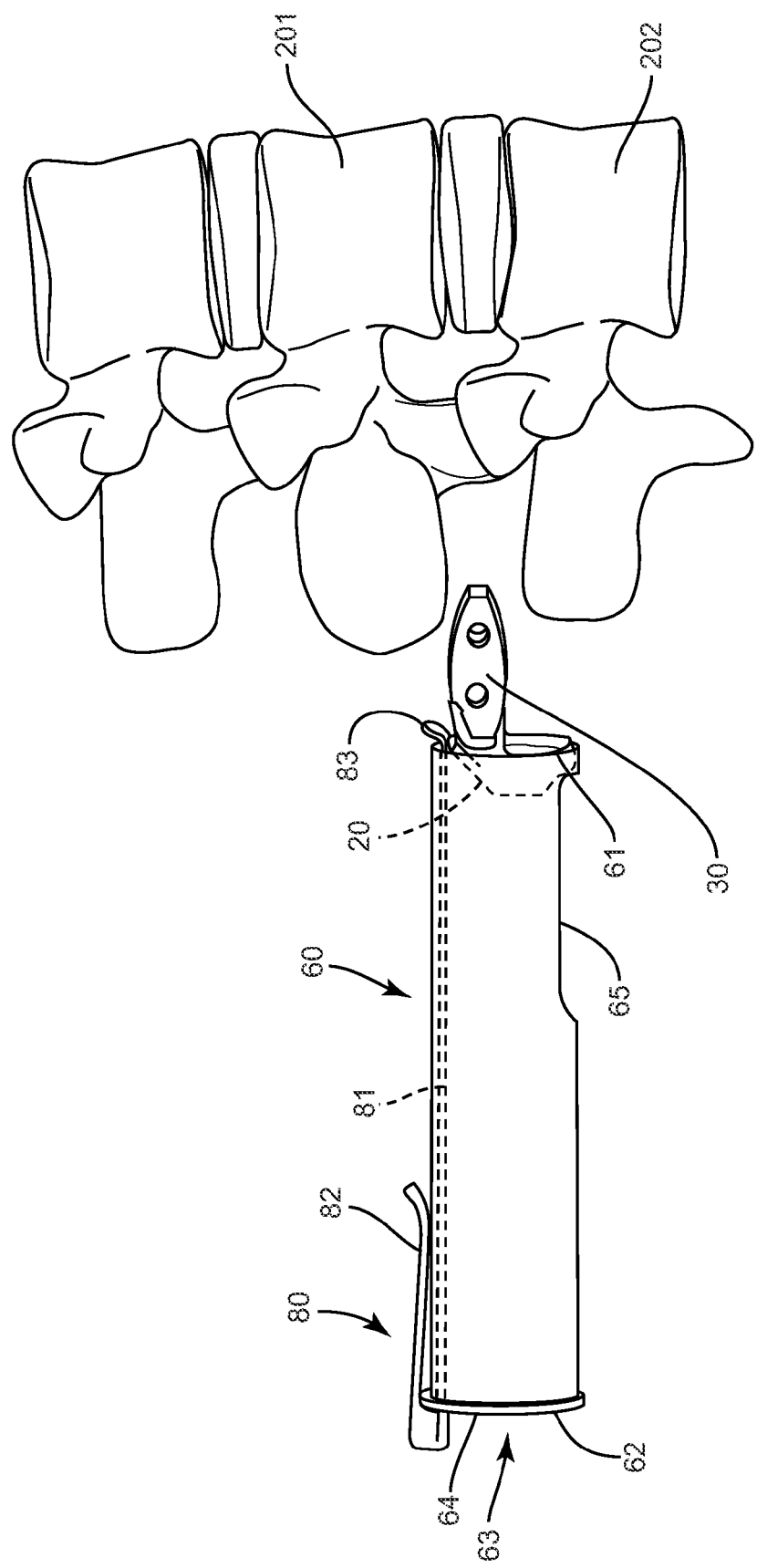
FIG. 7 is a side view of an insertion device and an implant extending outward from an end of the insertion device.

FIG. 7 illustrates an insertion device 60 that comprises an elongated tubular body with a distal end 61 and a proximal end 62. The device 60 may include various sizes. For example, the guide 60 may have an overall length of 4-10 cm and a width of 15-20 mm. The distal end 61 is configured to be positioned adjacent the spine, such as between the nerve root of a superior level vertebral member and the base of the pedicle of an adjacent inferior level vertebral member. The proximal end 62 is a positioned away from the spine and configured as a receiving end for receiving the implant 10 and/or tools. A working channel 63 extends through the device 60 for receiving the implant 10 or a tool. The guide 60 may include an oval cross-sectional shape, although other configurations are contemplated.

The guide 60 may include at least one aperture 65 that provides an access port to the channel 63. The apertures 65 may be positioned at various points on the guide 60, including superior or inferior positions of the guide 60. Various types of tools may be received within each aperture 65, such as an anchor 90 or screw driver inserted through an adjacent stab incision. The apertures 65 may have various shapes such as square, rectangular, circular or the like, and the shape is non-limiting.

The insertion device 60 may also include an attachment tab 64 that extends from the proximal end 62. The attachment tab 64 provides a support, such as for a secondary member, such as an electrical sensor, or electrode or the like. The secondary member may be one typically used in spinal fusion procedures, such as to monitor nerve conduction or to stimulate the nerve.

One example of a secondary member is a nerve root tool or probe 80 used to maneuver and protect an adjacent nerve root during the procedure. The nerve root tool 80 includes an elongated body portion 81 having a first end and a second end, and a retention portion 82. In this example, the retention portion 82 is a spring loaded clip extending from the first end of the body portion. The tool 80 may include a lip 83. In one embodiment, the tool 80 clips onto the guide 60 and extends through the working channel 63.

FIG. 7 illustrates the distal end 61 of the insertion device 60 spaced away from the vertebral members 201, 202 and the plate 20 and cage 30 extending outward beyond the distal end 61. Other methods of implantation include the distal end 61 placed in closer proximity to the vertebral members 201, 202 prior to the cage 20 and plate 30 being moved beyond the device 60.

Figure 8:
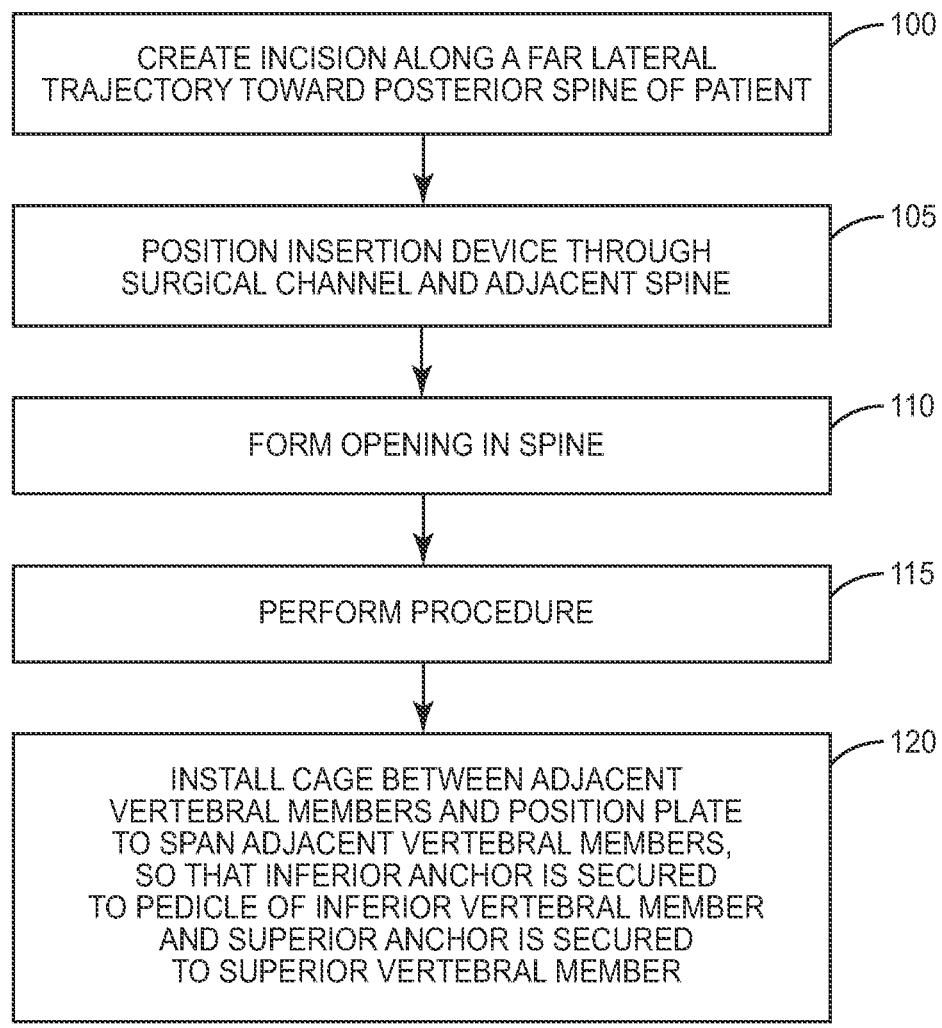
FIG. 8 is a flowchart of a method of implanting an implant within a patient.

Various methods may be used for implanting the implant 10 into the patient. FIG. 8 generally illustrates the steps of implantation. Advantageously, the methodology provides for a smaller incision and faster insertion. The low profile of the plate 20 allows for direct attachment to adjacent vertebral members. The methodology may be used in various applications, including with thoracic or lumbar spine trauma or tumor or other conditions. For example, the spinal fusion implant 10 can be implanted in between adjacent vertebral members via minimally invasive access to the posterior lumbar spine. The spinal fusion implant 10 may also be implanted in other areas of the lumbar, cervical, thoracic spine.

The methodology of this example contemplates a far lateral approach to the spine, although it may be configured for use in other techniques, such as a direct lateral approach of the lumbar spine, an anterior approach of the cervical spine, an anterior approach to the lumbar spine, anterolateral approaches of the lumbar spine, or anterolateral approaches of the thoracic spine, or the like.

Figure 9:
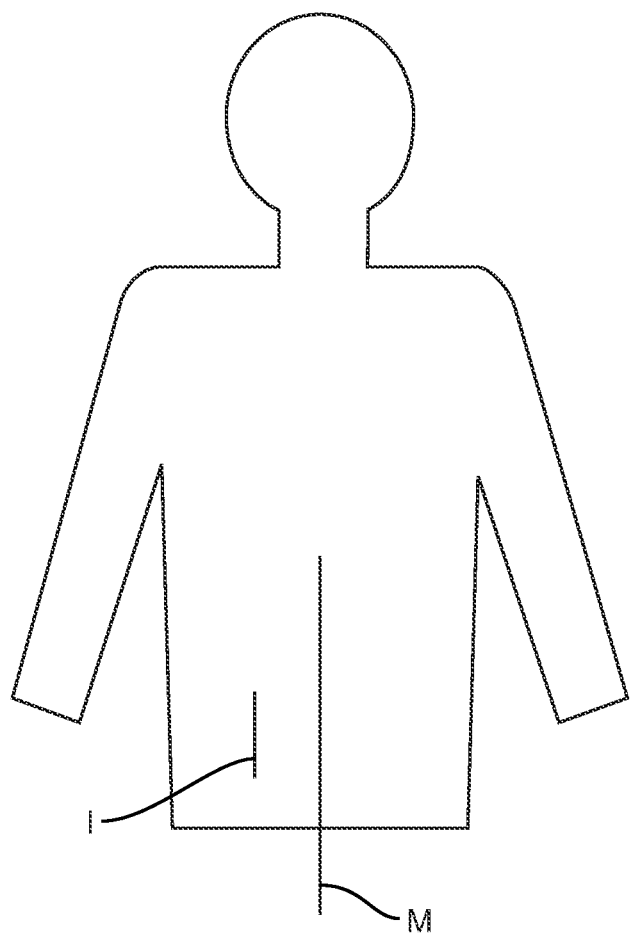
FIG. 9 is a schematic posterior lumbar view of an incision relative to a midline of a patient.

As illustrated in FIG. 8, the methodology begins with the step of forming an incision along a far lateral trajectory toward the posterior spine of the patient to create a surgical corridor (block 100). FIG. 9 schematically illustrates the position of the incision I relative to the midline M of the patient. An advantage of the far lateral approach is that the incision I may be smaller than in other insertion procedures. For example, the incision I may be a 22-24 mm incision 40-50 mm off the midline M of the patient. Another advantage is that a relative safe zone between the nerve root of a superior level vertebral member and the base of the pedicle of an adjacent inferior level vertebral member can be easily assessed.

Figure 10:
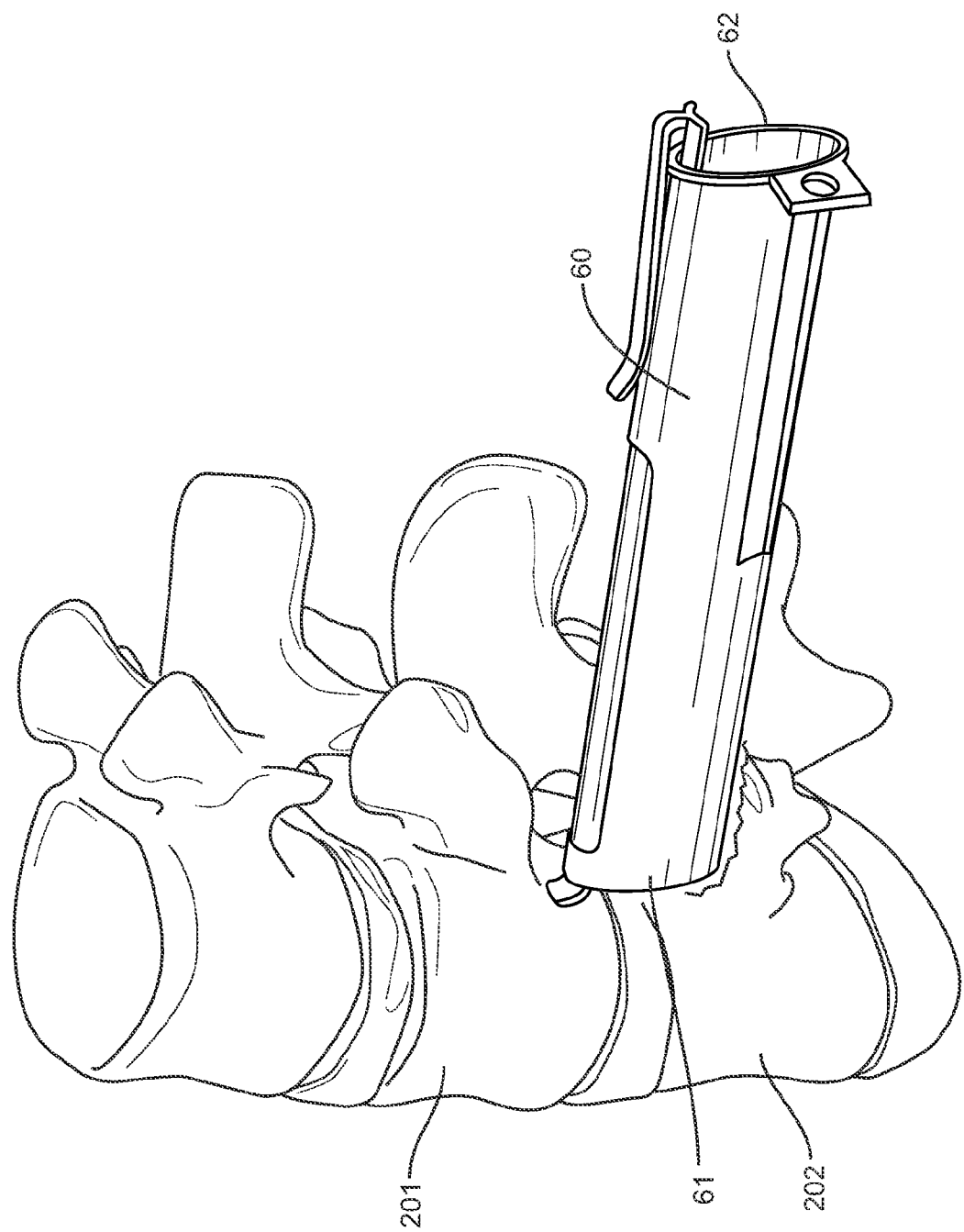
FIG. 10 is a perspective view of an insertion device positioned relative to vertebral members.

The insertion device 60 is then positioned within the patient through the incision (block 105). This positioning is further illustrated in FIGS. 10 and 11. The distal end 61 of the insertion device 60 is positioned adjacent the end plate of a superior vertebral member 201 and the base of the pedicle of an inferior vertebral member 202. If necessary, a nerve root retractor can be added to the insertion device 60 prior to insertion and manipulated to move an adjacent nerve root out of the way. Placement of the insertion device 60 may be accomplished via known techniques including use of a computer navigation guided K-wire through the surgical corridor, whereby the insertion device 60 is placed over the K-wire and extends through the surgical corridor to a predetermined position adjacent the spine. The nerve root retractor can be manipulated to protect the adjacent nerve root during placement of the insertion device.

The next step is forming an opening in the spine (block 110). For example, a drill or reamer is utilized to remove the facet joint and remove the superior portion of the inferior pedicle to create a bony corridor through the inferior pedicle/pars complex. This removal allows greater access to the intervertebral space than a typical transforaminal approach as the superior aspect of the inferior pedicle often blocks some access to the intervertebral space. Removal of the superior aspect of the inferior pedicle also provides an area where the plate 20 can sit adjacent to the dorsal aspect of the inferior vertebral body.

The method then includes performing other procedures, such as a diskectomy, decompression, or interbody arthrodesis of the endplates (block 115).

The methodology then includes implanting the plate 20 and cage 30 (block 120). The inferior anchor 90 may be secured to the pedicle of the inferior vertebral member. The superior anchor 90 may be secured to the superior vertebral member through the endplate or the endplate/vertebral body junction. The plate 20 and cage 30 may be inserted through the insertion device 60 separately, or they may be preassembled or partially assembled prior to insertion.

Figure 11:
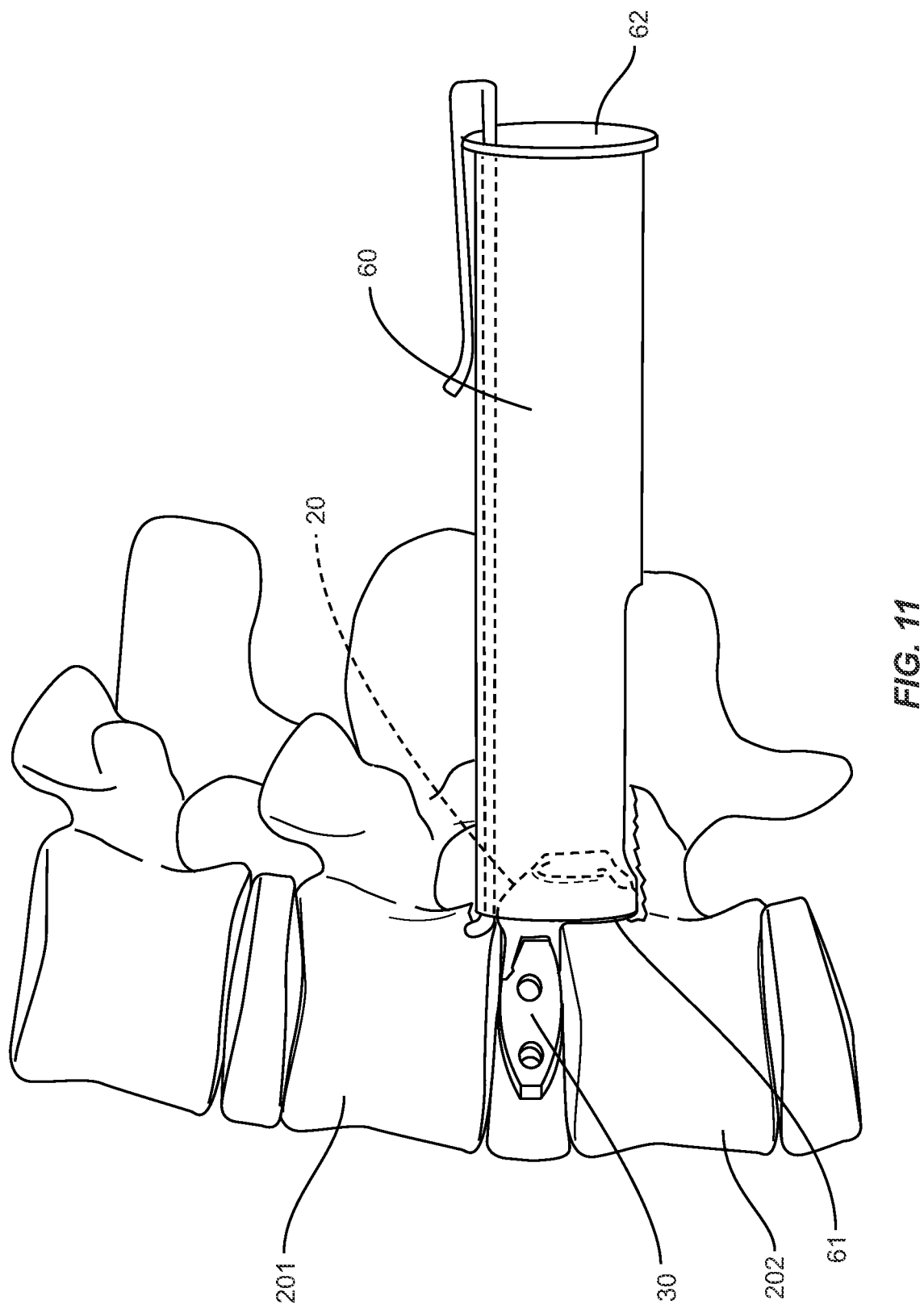
FIG. 11 is a side view of an insertion device positioned relative to vertebral members and an implant positioned at the vertebral members.
Figure 12:
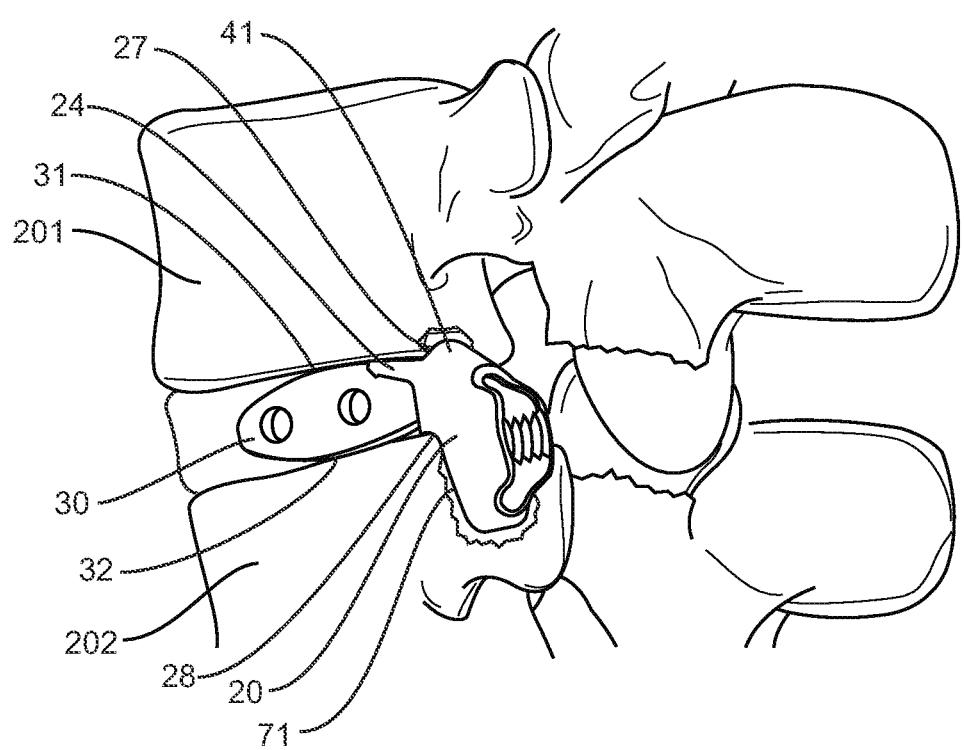
FIG. 12 is a perspective view of an implant positioned relative to vertebral members.
Figure 13:
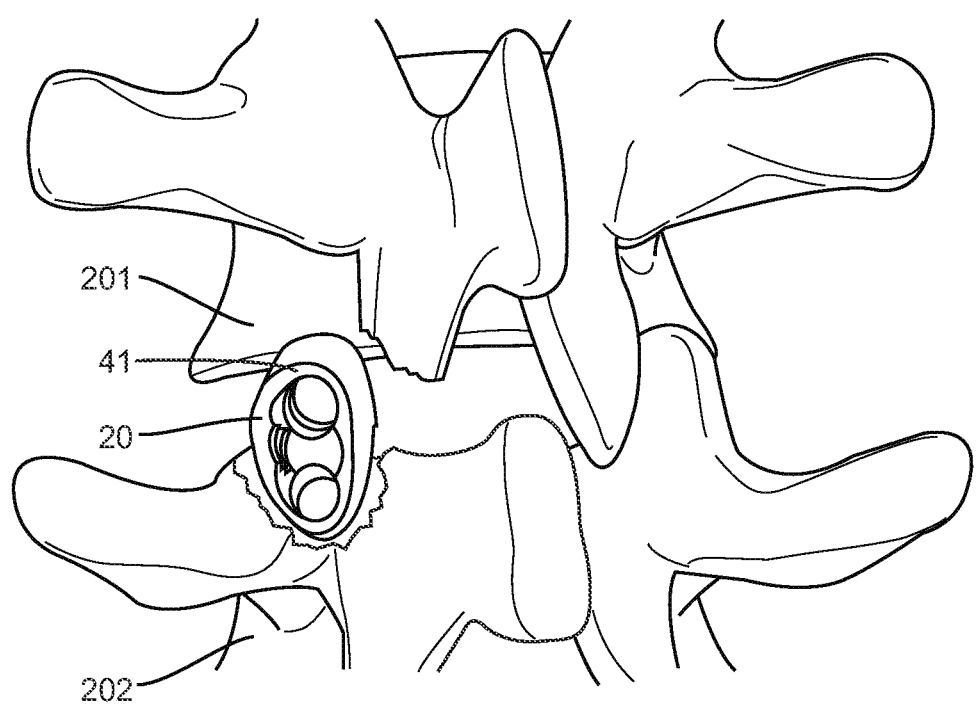
FIG. 13 is a posterior anatomic view of an implant positioned relative to vertebral members.
Figure 14:
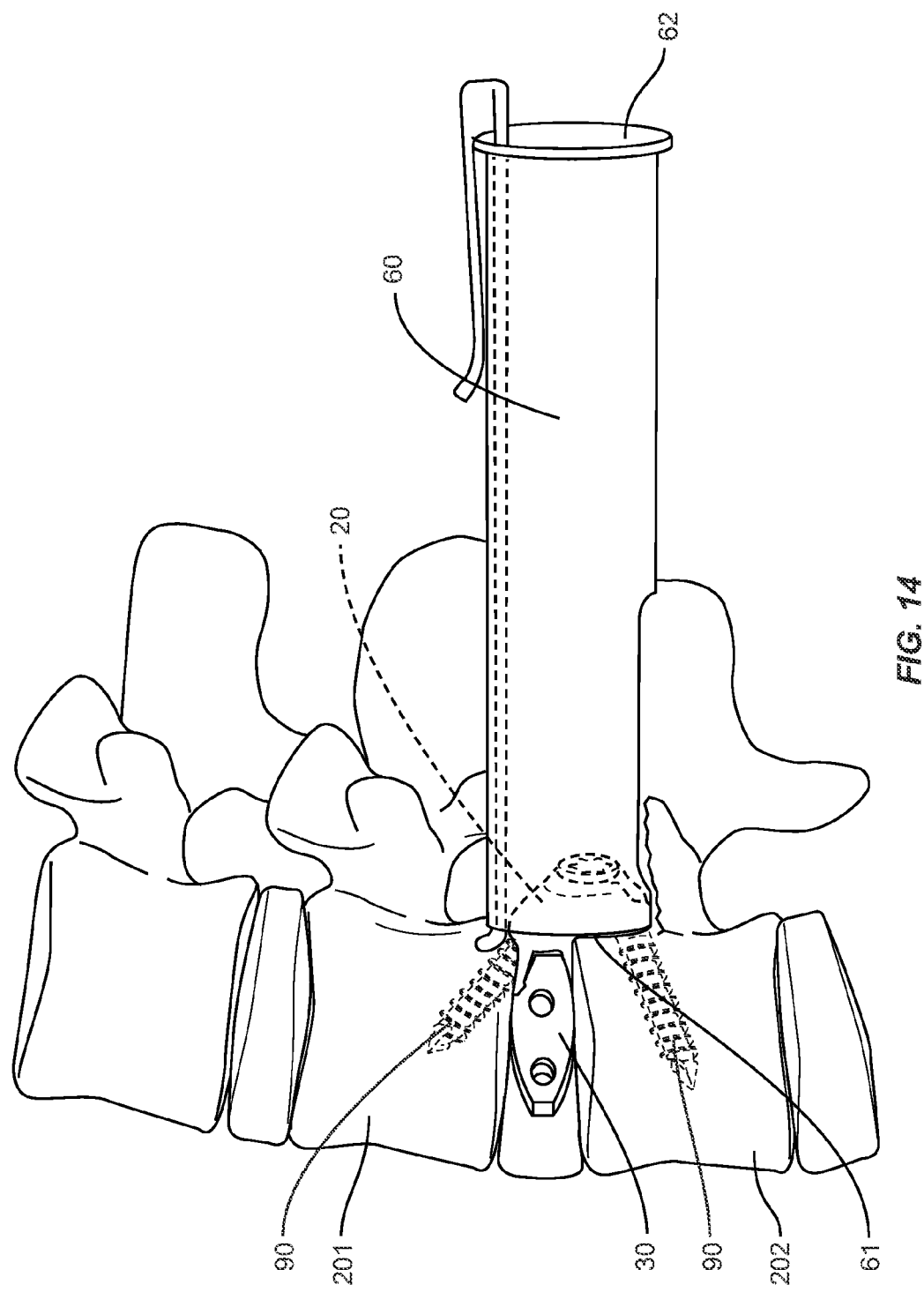
FIG. 14 is a side view of an insertion device positioned relative to vertebral members and an implant secured with anchors to the vertebral members.

FIGS. 11, 12, 13, and 14 illustrate the implant 10 positioned relative to the vertebral members 201, 202. FIGS. 11 and 14 include the insertion device 60 used for inserting the implant 10. For clarity purposes, the insertion device 60 is not illustrated in FIGS. 12 and 13.

The implant 10 is positioned to extend along the sides of the bodies of the vertebral members 201, 202 and to also be positioned within the intervertebral space between the vertebral members 201, 202. The plate 20 is positioned with the third plate section 72 at the superior end of the plate 20 being positioned against the body of the superior vertebral member 201. Further, the superior leg or legs 24 extend into the intervertebral space with the outer surfaces 50 contacting against or approximating to the endplate of the superior vertebral member 201. The rounded corner at the ledge 27 may abut against the edge of the superior vertebral member 201.

The second plate section 71 at the inferior end of the plate 20 is positioned against the body of the inferior vertebral member 201. Further, the inferior leg or legs 24 extend into the intervertebral space with the outer surfaces 50 contacting against the endplate of the inferior vertebral member 202. The rounded corner of the ledge 28 may abut against the edge of the inferior vertebral member 202.

The inner side 23 of the plate 20 is configured for a portion of the plate 20 between the ledges 27, 28 to be positioned within the intervertebral space. This positioning helps to give the plate 20 a low profile.

The plate 20 is positioned with the contoured superior section 41 positioned to minimize contact with the exiting and traversing nerve root. The superior section 41 includes a tapered shape. As illustrated in FIG. 13, the superior section also includes a rounded shape.

The cage 30 extends outward from the plate 20 in the intervertebral space. The first side 31 contacts against the endplate of the superior vertebral member 201 and the second side 32 contacts against the endplate of the inferior vertebral member 202.

Figure 15:
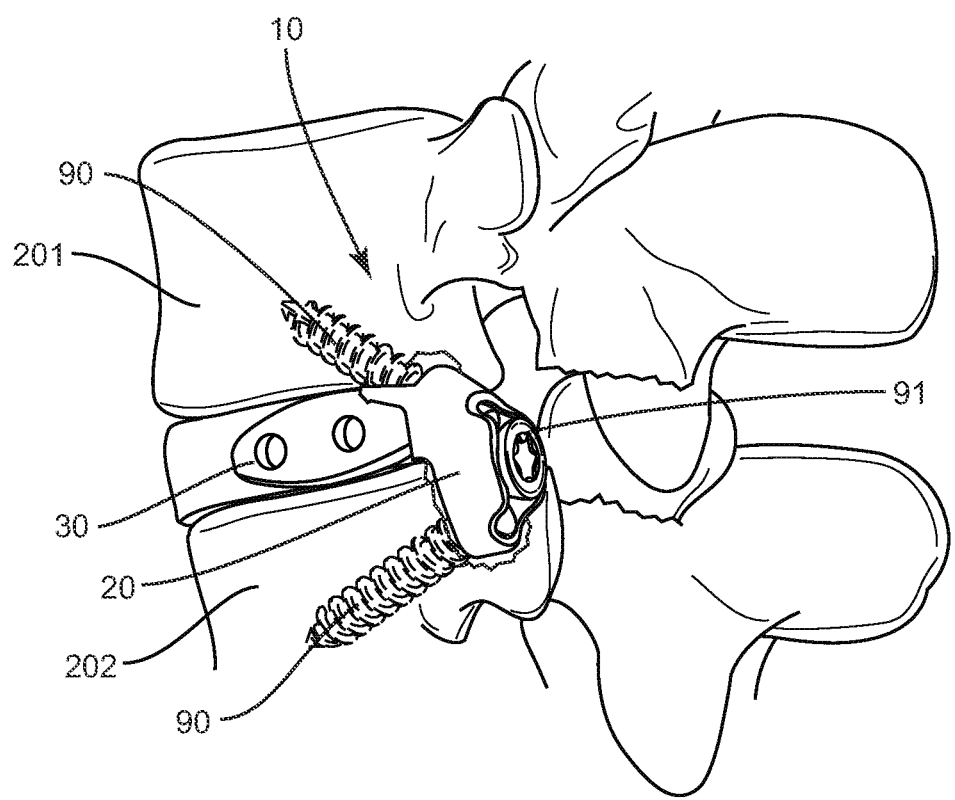
FIG. 15 is a perspective view of an implant secured with anchors to the vertebral members.

As illustrated in FIGS. 14 and 15, one or more anchors 90 secure the implant 20 to the vertebral members 201, 202. An inferior anchor 90 is positioned through an aperture 26 in the plate 20 and into the remains of the pedicle of the inferior vertebral member 202. A superior anchor member 90 is positioned through an aperture 26 in the plate 20 and into the adjacent vertebral body/endplate junction of the superior vertebral member 201. A superior anchor 90 may also extend through the pedicle of the superior vertebral member 202. Various numbers of anchors 90 may be used secure the implant 10 within the patient.

The anchors 90 may be inserted directly through the channel 63 of the insertion device 60, or through the one or more apertures 65 formed in the insertion device 60, such as through an adjacent stab incision.

A securing device 91 is attached to the plate 20 to prevent back-out of the anchors 90. The securing device 91 thus locks the anchors 90 in place to prevent migration of the anchors 90.

It is forseeable that a longer inferior anchor 90 could be used to affix the implant 10 with a conventional rod and screw construction. In this configuration, the lower anchor 90 would extend toward and attach to an adjacent level's rod. In one embodiment, as the superior anchor 90 is placed in the adjacent vertebral body, the leg 24 of the plate 20, and in particular the gripping feature 25 on the end of the leg 24, tightens or locks around the cage 30 through compressive forces. As a result, the plate 20 and cage 30 are locked together.

The implant 10 is positioned between the bodies of the vertebral members 201, 202 and the lamina/pars/facet joint. This positioning provides a low profile that does not protrude from the dorsal part of the lamina/pars/facet joint like other forms of posterior fixation such as pedicle screws and rods/plates or spinous process plates.

Figure 16:
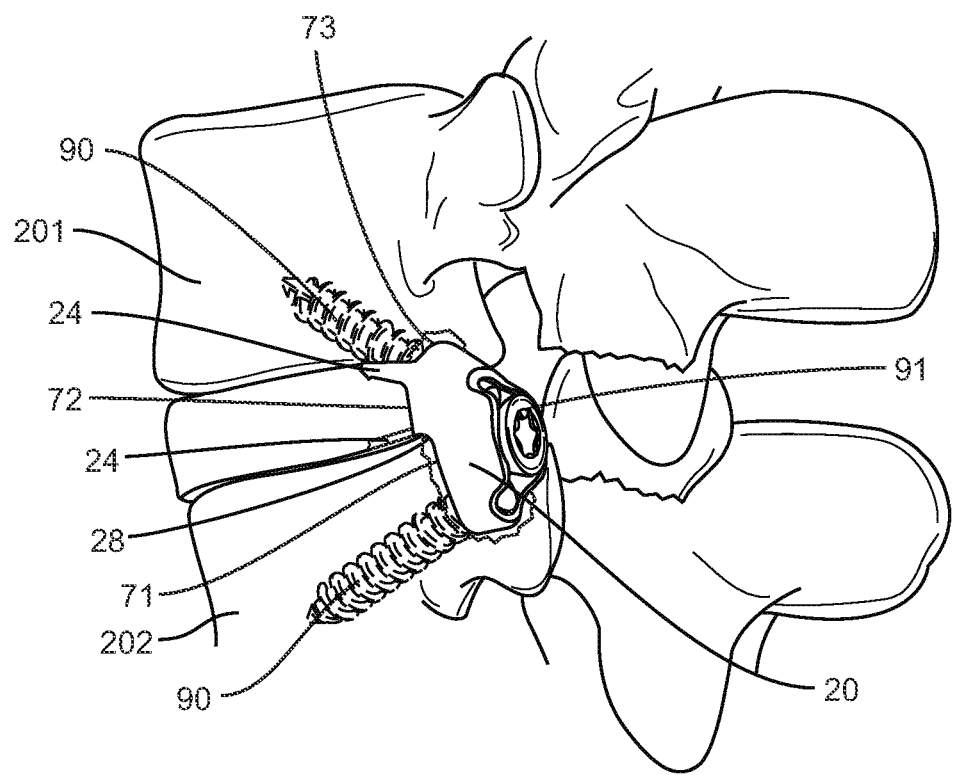
FIG. 16 is a perspective view of a plate secured with anchors to the vertebral members.

The implant 10 described above includes both the plate 20 and the cage 30. The plate 20 may be used alone without the cage 30, or with a cage that is not connected to the plate 20. FIG. 16 illustrates one embodiment of the plate 20 used without the cage 30. A portion of the plate 20 extends into the intervertebral space to space apart the vertebral members 201, 202. The superior leg or legs 24 contact against the endplate of the superior vertebral member 201 and the inferior leg or legs 24 contact against the endplate of the inferior vertebral member 202. The legs 24 may act to position the plate 20 or center the plate 20 inferiorly/superiorly within the intervertebral space and relative to the vertebral members 201, 202. The plate 20 may be secured with one or more anchors 90 as explained above.

The implants 10 described above offer various advantages. The various implants 10 can be uniformly inserted anywhere in the vertebral column for use in a variety of different spinal pathologies including degeneration, trauma, tumor, infection, or congenital abnormalities. Yet another advantage is that the implants 10 mitigate tissue destruction, increases surgical implant speed, have more stable biomechanical properties, enables easy reversibility, requires less equipment in an operating room to implant and/or stored in sterile containers, enables the utilization of a variety of graft configurations, and ultimately lowers costs. Yet a further advantage is that the implants 10 are multifunctional.

Figure 1:
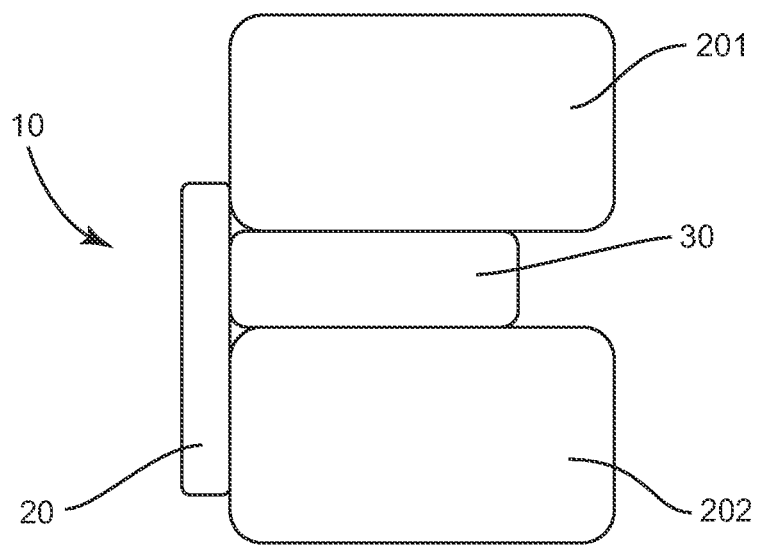
FIG. 1 is a schematic view of an implant attached to vertebral members.
Figure 17:
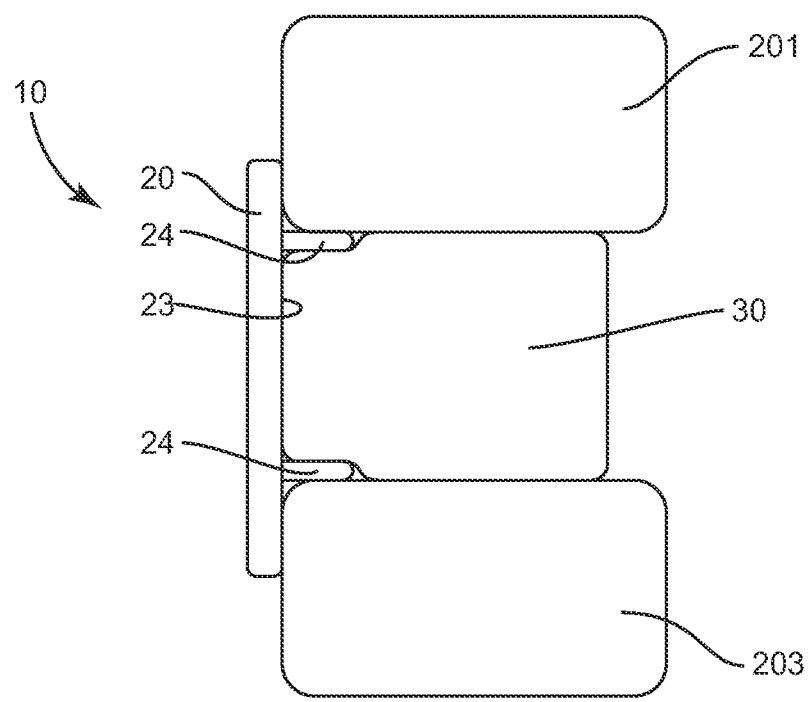
FIG. 17 is a schematic view of an implant attached to vertebral members.

The device 10 may be sized to accommodate a variety of different anatomical spaces. FIG. 1 includes the device 10 with a plate 20 sized to extend across a disc space between adjacent vertebral members 201, 202 with the cage 30 positioned within the intervertebral disc space. The plate 20 may also be sized for a larger space as illustrated in FIG. 17. The larger space may be formed when an intermediate vertebral member (i.e., vertebral member 202) is removed during a corpectomy procedure. The plate 20 includes a length to position a superior portion over the vertebral member 201 and an inferior portion over vertebral member 203. One or more legs 24 may extend outward from the second side 23 to position the plate 20 within the space. FIG. 17 includes the plate 20 having superior and inferior legs 24. Other embodiments may include a single leg.

A cage 30 is operatively connected to the plate 20 and positioned within the space between the vertebral members 201, 203. A superior side of the cage 30 is positioned to contact against the vertebral member 201, and an inferior side contacts against vertebral member 203. One or more anchors (not illustrated) may extend through the cage 30 and/or plate 20 to secure the device 10. One or more securing devices 91 secure the anchor(s) 90 to the plate 20. In one embodiment, a first securing device 91 extends over and secures a first anchor 90 to vertebral member 201 and a second securing device 91 extends over and secures a second anchor 90 to vertebral member 203.

The enlarged device 10 may be inserted into the patient using a variety of different approaches. The posterior approaches described above may also be applicable to the larger device. In another procedure used on the thoracic spine, the device 10 is inserted into the patient using a lateral extracavitary approach.

The implant 10 may be used during surgical procedures on living patients. The implant 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A vertebral implant for attaching to superior and inferior vertebral members, the implant comprising:
   a plate extending along an axis between a first end surface and an opposite second end surface, the plate comprising an inner side configured to be positioned towards the vertebral members, the inner side defining a first contact section configured to contact against a body of the superior vertebral member and a second contact section coaxial with the first contact section configured to contact against a body of the inferior vertebral member;
   a plurality of legs that each extend outward from and are spaced apart along the inner side, each of the legs sized to fit within an intervertebral space formed between the vertebral members, the plurality of legs spaced apart along the inner side by a gap;
   a ledge formed at the second contact section and positioned away from a gap formed between the plurality of legs, the ledge extending outward beyond the second contact section and configured to contact against an endplate of the inferior vertebral member, the second contact section having a length defined by a distance between the second end surface and the ledge, the second contact section being continuously parallel to the axis and being continuously planar along the length;
   at least one aperture that extends through the second contact section to receive an anchor; and
   a cage positioned in the gap between the legs and extending outward from the inner side of the plate and configured to fit within the intervertebral space.

2. The vertebral implant of claim 1, wherein one of the plurality of legs includes an outer surface that faces away from the gap and is aligned with the ledge and is configured to contact against the endplate of the inferior vertebral member.

3. The vertebral implant of claim 1, wherein the first inner side further includes a third contact section positioned in the gap to contact against the cage, the third contact section being misaligned with the first and second contact sections and positioned outward toward the cage more than the first and second contact sections.

4. The vertebral implant of claim 1, wherein the plate further includes a superior side and an inferior side, the superior side including a tapered and curved shape that is aligned with the first contact section.

5. The vertebral implant of claim 1, wherein the plurality of legs includes a pair of legs laterally spaced apart at a first location along the inner side and an opposing single leg at a second location along the inner side, the single leg being wider than each of the pair of legs.

6. The vertebral implant of claim 1, wherein each of the plurality of legs includes a tab that extends from an inner side towards the gap, the tabs including a tapering width that terminates at a ledge configured to engage with the cage.

7. The vertebral implant of claim 1, wherein the plate further comprises an outer side opposite from the inner side, the outer side including a recess that extends towards the inner side and including a superior aperture configured to receive a first anchor and an inferior aperture configured to receive a second anchor, the superior and inferior anchors being spaced apart within the recess.

8. The vertebral implant of claim 7, wherein the recess includes a threaded receptacle positioned over the superior and inferior apertures to receive a threaded locking device configured to engage with the receptacle and extend over the first and second apertures.

9. The vertebral implant of claim 1, wherein an inner surface of the plate defines a cavity and the at least one aperture includes first and second apertures positioned within the cavity each configured for disposal of an anchor, the cavity further including a hole that at least partially overlaps the first and second apertures configured for disposal of a locking device to prevent the anchors from backing out of the first and second apertures.

10. The vertebral implant of claim 1, wherein at least two of the legs are angled in opposing directions.

11. A vertebral implant for attaching to first and second vertebral members, the implant comprising:
    a plate extending along an axis between a first end surface and an opposite second end surface, the plate comprising an inner side configured to be positioned towards the vertebral members and an opposing outer side, the plate also including a superior side configured to be positioned along the first vertebral member and an opposing inferior side configured to be positioned along the second vertebral member;
    first and second elbows positioned on the inner side and each including a first face configured to contact against a body of one of the vertebral members and a second face that extends outward from the first face and away from the outer side of the plate to contact against an endplate of one of the vertebral members, the first faces being coaxial, the first face of the second elbow having a length defined by a distance between the second end surface and the second face of the second elbow, the first face of the second elbow extending continuously parallel to the axis and being continuously planar along the length of the first face of the second elbow, the elbows being spaced apart along the inner side by a gap and oriented in opposing directions with the second face of the first elbow facing towards the first end surface of the plate to face towards an endplate of the first vertebral member and the second face of the second elbow facing towards the inferior side of the plate to face towards an endplate of the second vertebral member;
    a first protrusion extending outward from the inner side of the plate, the first protrusion positioned in the gap and including an outer surface that aligns with a surface of the first elbow to face towards the endplate of the first vertebral member;
    a second protrusion extending outward from the inner side of the plate, the second protrusion positioned in the gap and including an outer surface that aligns with a surface of the second elbow to face towards the endplate of the second vertebral member;
    an aperture that extends through the plate to receive an anchor to attach the plate to one of the first and second vertebral members; and a cage positioned between the protrusions and having a length to extend outward from the inner side of the plate beyond the protrusions and being configured to fit within the intervertebral space.

12. The vertebral implant of claim 11, wherein each of the elbows further includes a rounded transition between the first face and the second face.

13. The vertebral implant of claim 11, wherein the first protrusion includes a pair of legs that are laterally spaced apart at a common location along the inner side.

14. The vertebral implant of claim 11, wherein the first end surface of the plate includes a more tapered shape than the second end surface of the plate.

15. The vertebral implant of claim 11, further comprising a recess that extends into the outer side of the plate with the aperture positioned at a bottom of the recess.

16. The vertebral implant of claim 11, wherein each of the protrusions includes a tab that extends from an inner surface and includes a tapering width that terminates at a ledge configured to engage with the cage.

17. A vertebral implant for attaching to first and second vertebral members, the implant comprising:
- a plate extending along an axis between a first end surface and an opposite second end surface, the plate comprising an inner side configured to be positioned towards the vertebral members and an opposing outer side, the plate also including lateral sides that extend between the first and second end surfaces with the plate having a greater length measured between the superior and inferior sides than a width measured between the lateral sides;
- first and second elbows positioned on the inner side and spaced apart along the length, each of the elbows including a first face configured to contact against a body of one of the vertebral members and a second face that extends outward from a first face of the plate to face towards an endplate of one of the vertebral members when the plate is implanted in the patient, the first faces being coaxial, the first face of the second elbow having a length defined by a distance between the second end surface and the second face of the second elbow, the first face of the second elbow extending continuously parallel to the axis and being continuously planar along the length of the first face of the second elbow, the elbows being oriented in opposing directions with the second face of the first elbow facing towards the superior side first end surface of the plate and the second face of the second elbow facing towards the second end surface of the plate;
- a first protrusion extending outward from the inner side of the plate, the first protrusion positioned between the elbows and including an outer surface that aligns with a second contact surface of the first elbow to face towards the endplate of the first vertebral member;
- a second protrusion extending outward from the inner side of the plate, the second protrusion positioned between the elbows and including an outer surface that aligns with the second contact surface of the second elbow to face towards the endplate of the second vertebral member;
- an aperture that extends through the plate from the outer side to the inner side to receive an anchor to attach the plate to one of the first and second vertebral members.

18. The vertebral implant of claim 17, wherein each of the elbows further includes a rounded transition between the first face and the second face.

19. The vertebral implant of claim 17, wherein the first protrusion includes a pair of legs that are laterally spaced apart at a common location along the width.

20. The vertebral implant of claim 17, further comprising a recess that extends into the outer side of the plate with the aperture positioned at a bottom of the recess.

* * * * *